United States Patent [19]
Schlarb et al.

[11] Patent Number: 5,989,630
[45] Date of Patent: Nov. 23, 1999

[54] POLYMERS HAVING MORE THAN ONE VOID

[75] Inventors: Bernhard Schlarb, Ludwigshafen; Elmar Schwarzenbach, Römerberg; Walter Heckmann, Weinheim, all of Germany

[73] Assignee: BASF Aktiengesellschaft, Ludwigshafen, Germany

[21] Appl. No.: 09/035,875

[22] Filed: Mar. 6, 1998

[30] Foreign Application Priority Data

Mar. 7, 1997 [DE] Germany .......................... 197 09 490

[51] Int. Cl.⁶ .................. C08J 9/20; A61F 9/50; C08F 291/00
[52] U.S. Cl. .................. 427/213.36; 427/213.3; 427/213.31; 427/213.34; 264/45.1; 264/45.3
[58] Field of Search .................. 427/213.3, 213.31, 427/213.34, 213.36; 264/45.1, 45.3

[56] References Cited

U.S. PATENT DOCUMENTS 5,173,523  12/1992  Auchter et al. .

FOREIGN PATENT DOCUMENTS 0 225 612   6/1987   European Pat. Off. .

*Primary Examiner*—Nathan M. Nutter
*Attorney, Agent, or Firm*—Oblon, Spivak, McClelland, Maier & Neustadt, P.C.

[57] ABSTRACT

Disclosed are a polymer in the form of particles more than 1 μm in size which contain more than one void, an aqueous dispersion comprising this polymer, processes for the preparation thereof and the use thereof.

9 Claims, No Drawings

POLYMERS HAVING MORE THAN ONE VOID

The present invention relates to a polymer in the form of particles more than 1 µm in size which have more than one void, to an aqueous dispersion comprising this polymer, to processes for the preparation thereof and to the use thereof.

Polymers, mostly in the form of aqueous dispersions, with voids are known per se and have been used for some years, including as opacifying white pigments instead of titanium dioxide.

Particles having only one void in the core are described, inter alia, in U.S. Pat. Nos. 4,427,836 and 4,469,852 and 4,594,363.

Polymer particles having a plurality of voids are likewise known.

For instance, JP 08 89 789 describes the production of hollow resin particles as replacement for $Tio_2$ by mixing a self-dispersible resin, an immiscible hydrophobic substance and an organic solvent, emulsifying this mixture so that the hydrophobic substance comes to be located within the resulting resin particles, and then extracting the hydrophobic substance using a suitable solvent. This method yields particles 0.5 µm in diameter.

U.S. Pat. No. 4,968,562 describes acid-free polymer particles having more than one void, comprising (a) at least about 70 parts by weight of at least one alkyl acrylate or alkyl methacrylate ester and (b) up to 30 parts by weight of at least one nitrogen-containing polar monomer. The exemplified polymer particles have voids about 2 µm in diameter and are crosslinked in the course of their formation.

EP-A 0 408 189 describes particles of a hydrophobic polymer which have at least one void and comprise an essentially hydrophobic surface-active component and an essentially hydrophilic surface-active component. The hydrophobic surface-active component used therein is a more particularly defined block copolymer having a hydrophilic content of from 5 to 45% by weight, where the hydrophilic surface-active component described therein is characterized inter alia in that the hydrophilic content of this component is from 40 to 90% by weight.

Okubo et al. describe a further process for preparing latex particles having many voids, wherein styrene/butyl acrylate/methacrylic acid terpolymers are treated first with bases and then with acids (see Colloid Polym. Sci. 269 (1991), 1257–1262). The process of this reference is disadvantageous in that large amounts of surfactants have to be used to stabilize the dispersion. In addition, the polymer particles obtained according to this reference are distinctly less than 1 µm in size.

A further method for preparing latex particles having many voids, this method being based on an extraction process, is described by Okubo et al. in Colloid Polym. Sci. 272 (1994), 530–535. A mixture of styrene and divinylbenzene is polymerized in the presence of an initial charge of uncrosslinked polystyrene particles. Extraction of the uncrosslinked polystyrene with toluene leaves monodisperse, crosslinked particles having many voids. Polyacrylic acid is used as hydrophilic component for stabilization. Furthermore, the particles are crosslinked. The particular disadvantage of the process described is the time-consuming extraction, which can take from several days up to 2 weeks.

Commonly assigned EP-A 0 225 612 describes aqueous polymer dispersions whose polymer content is similar in terms of composition to the polymer claimed herein. According to the examples of this reference, the polymerization is likewise carried out in an organic yet water-miscible solvent, eg. ethanol or isobutanol. Particles are obtained with a core-shell structure and a diameter which is generally less than 1 µm.

It is clear from the above that there are already existing processes for preparing polymers in the form of particles having more than one void, and also such particles per se.

However, these polymers are not satisfactory in all their properties, variously lacking stability, void number or void size for optimum utility as a pigment. The processes are variously disadvantageous in that they are technically complicated, time-consuming or involve the use of significant quantities of organic solvents.

It is an object of the present invention to provide a polymer which has more than one void, which is highly suitable for use as a white pigment in particular and which can exist in a stable form as an aqueous dispersion which is free of organic stabilizers. Furthermore, the polymer in question shall be producible substantially free of organic solvents.

We have found that this object is achieved by the present invention by a polymer in the form of particles which are more than 1 µm in size and have more than one void, consisting essentially of the components.

A) from 25 to 70% by weight of a copolymer A containing
  I) from 5 to 50% by weight of at least one copolymerizable monomer containing at least one hydrophilic group,
  II) from 20 to 95% by weight of at least one copolymerizable monomer which is free of hydrophilic groups,
  III) from 0 to 30% by weight of at least one other copolymerizable compound,
  the percentages mentioned under I) to III) adding up to 100,
B) from 30 to 75% by weight of a solution polymer B containing from 0 to less than 5% by weight of the above monomer I,
obtainable by a process comprising the following steps:
  α) solution polymerization of one of said components (A) or (B) in an organic solvent and subsequent solution polymerization of the other component in the resulting polymerization solution, the solution polymerization being carried out in a water-immiscible solvent or solvent mixture,
  β) dispersing the solution comprising (A) and (B) in water in the presence of a base, and
  γ) distillative removal of the organic solvent down to a concentration of less than 5% by weight, based on the amount of the dispersion.

The present invention further provides an aqueous dispersion comprising the above polymer.

The present invention further provides a process for preparing an aqueous dispersion as defined above, comprising the following steps:

α) solution polymerization of one of said components (A) or (B) in an organic solvent and subsequent solution polymerization of the other component in the resulting polymerization solution, the solution polymerization being carried out in a water-immiscible solvent or solvent mixture,
  β) dispersing the solution comprising (A) and (B) in water in the presence of a base, and
  γ) distillative removal of the organic solvent down to a concentration of less than 5% by weight, based on the amount of the dispersion.

The present invention further provides a process for preparing a polymer as defined above in the form of a solid, comprising the following steps:

α) solution polymerization of one of said components (A) or (B) in an organic solvent and subsequent solution polymerization of the other component in the resulting polymerization solution, the solution polymerization being carried out in a water-immiscible solvent or solvent mixture, β) dispersing the solution comprising (A) and (B) in water in the presence of a base, and γ) distillative removal of the organic solvent down to a concentration of less than 5% by weight, based on the amount of the dispersion, and δ) subsequent drying of the dispersion.

The polymer of the present invention is a polymer mixture of a copolymer which is rich in hydrophilic groups and a solution polymer which is lean in or completely devoid of hydrophilic groups.

The polymer is generally present in the form of particles more than 1 to about 50, preferably more than 1 to about 10, especially from about 3 to about 6, $\mu$m in size.

The void size is freely selectable, provided it ensures that there is more than one void per particle. Preferably, however, the diameter of the voids which are present is within the range from about 400 to about 800 nm, ie. essentially within the region of the wavelength of visible light.

The polymer mixture obtained preferably has a glass transition temperature which is above room temperature, more preferably within the range from about 40° C. to about 150° C., especially within the range from about 60° C. to 110° C., since it is then possible for a previously formed structure to be locked in at room temperature.

The polymer of the present invention consists essentially of from about 25 to about 70%, preferably from about 40 to about 60%, especially from about 45 to about 55%, by weight of a copolymer A and from about 30 to about 75%, preferably from about 40 to 60%, especially from about 45 to about 55%, by weight of a solution polymer B, the percentages mentioned under (A) and (B) adding up to 100.

Component (A) is a copolymer containing

I) from about 5 to about 50%, preferably from about 10 to about 30%, especially from about 10 to about 20%, by weight of at least one copolymerizable monomer containing hydrophilic groups, II) from about 20 to about 95%, preferably from about 50 to about 90%, by weight of a copolymerizable monomer which is free of hydrophilic groups, and III) from 0 to about 30%, preferably from 0 to about 20%, by weight of at least one other copolymeriz-able compound, the percentages mentioned under (I) to (III) adding up to 100.

Component (B) is a solution polymer essentially free of hydrophilic groups, and it comprises from 0 to about 5% by weight, preferably from 0 to about 3% by weight, especially, no copolymerizable hydrophilic monomer (I). Accordingly, component (B) consists in particular of monomers (II) and/or (III) only.

The above-defined polymer is prepared by initially polymerizing one of the two components (A) and (B) in an organic solvent and then polymerizing the other component (A) or (B) in the resulting polymer solution. It is also possible to polymerize one of the components (A) or (B) in an organic solvent and to introduce the other component in the resulting polymer solution as a separately prepared polymer.

Component (B) is by itself not water-thinnable and contains only small amounts, if any, of a hydrophilic monomer as defined above.

The monomers of components (A) and (B) will now be more particularly described:

Monomer (I) is suitably in particular a copolymerizable olefinically unsaturated carboxylic acid or anhydride containing up to 10 carbon atoms, for example acrylic acid, methacrylic acid, maleic acid, itaconic acid or an anhydride or monoester of these dicarboxylic acids. The anhydride groups of the copolymers can be converted into the corresponding monoester and monoamide groups, for example by heating with $C_1$–$C_8$ alcohols or glycol ethers and amines, respectively, prior to neutralization. Examples of such alcohols and glycol ethers are ethanol, isopropanol, butanol and butylglycol. Examples of amines are $NH_3$, primary amines, eg. butylamine, and secondary amines, eg. diethylamine. Mixtures of two or more of the above monomers can also be used.

Furthermore, it is possible to use copolymerizable olefinically unsaturated sulfonic acids, eg. 3-sulfopropyl(meth) acrylic acid or 2-acrylamido-2-methylpropanesulfonic acid, or a derivative thereof, copolymerizable olefinically unsaturated sulfates, copolymerizable olefinically unsaturated phosphoric acids or a derivative thereof, for example the phosphoric ester of hydroxyethyl (meth)acrylate, or copolymerizable olefinically unsaturated phosphonic acids or a derivative thereof, for example vinylphosphonic acid or mixtures thereof.

Acrylic acid, methacrylic acid and itaconic acid are particularly preferred monomers (I).

Suitable Monomers (II) are:

esters of acrylic acid or methacrylic acid with straight-chain or branched-chain monoalkanols containing from 1 to 20 carbon atoms, eg. methyl acrylate, ethyl acrylate, isopropyl acrylate, methyl methacrylate, n-butyl acrylate, n-butyl methacrylate, isobutyl acrylate, isobutyl methacrylate, tert-butyl acrylate, 2-ethylhexyl acrylate, 2-ethylhexyl methacrylate, lauryl acrylate and also mixtures thereof, particular preference being given to n-butyl acrylate and methyl methacrylate;

aromatic vinyl compounds which may be substituted, on the aromatic ring especially, one or more times by at least one alkyl radical and/or halogen and/or at least one amino radical, eg. vinyltoluene, styrene, α- and p-methylstyrene, α-butylstyrene, 4-n-butylstyrene, 4-n-decylstyrene, of which styrene is preferred.

It is also possible to use mixtures of two or more thereof.

Monomer (III) is a copolymerizable olefinically unsaturated compound other than those mentioned under (I) and (II).

Examples are:

vinyl esters of carboxylic acids having from 1 to 20 carbon atoms, eg. vinyl laurate, vinyl stearate, vinyl propionate and vinyl acetate; mono(meth)acrylates of alkanediols, eg. hydroxyethyl (meth)acrylate, hydroxypropyl (meth)acrylate and also butanediol mono (meth)acrylate; amides such as, for example, (meth) acrylamide;

vinyl ethers, vinyl esters, diesters of maleic acid, itaconic acid, citraconic acid or mesaconic acid with monoalcohols having from 1 to 20 carbon atoms and optionally containing ether or thioether groups; nitriles, eg. acrylonitrile and methacrylonitrile;

vinyl halides, ie. chlorine-, fluorine- or bromine-substituted ethylenically unsaturated compounds, eg.

vinyl chloride or vinylidene chloride; nonaromatic hydrocarbons having from 2 to 8 carbon atoms and one or two olefinic double bonds, eg. butadiene, isoprene, chloroprene, ethylene, propene, butene, pentene, hexene, isobutene; diolefins, eg. butadiene and isoprene; and also mixtures of two or more thereof.

As is apparent from the above, the preference is for no emulsifier to be used for the purposes of the present invention, although the use of commercially available emulsifiers is not ruled out.

With regard to solvents useful in the context of the process of the present invention, there are no restrictions whatsoever, as long as the solvent used is not miscible with water, ie. has a miscibility gap with the medium, at the polymerization temperature.

Suitable solvents of this type include in particular aromatic hydrocarbons, eg. toluene or xylene; aliphatic hydrocarbons, eg. n-hexane, n-heptane, isooctane and n-octane; cycloaliphatic hydrocarbons, eg. cyclohexane; or mixtures of two or more thereof. Particularly good results are obtained when the organic solvent used is a mixture between a good solvent for the polymer in question, eg. toluene, and a very poor solvent (coagulant) for the polymer, eg. n-octane; the mixture of toluene and n-octane in particular is particularly advantageous to use, the best results being obtained with a toluene to n-octane ratio which is within the range from about 5:1 to about 1:1.

The polymerization is advantageously carried out in the presence of from about 0.3 to about 5.0%, preferably from about 0.5 to about 3.0%, by weight, based on the sum total of monomers (I) to (III), of free-radical initiators, for example azobiscarboxamides, azobiscarbonitriles or peroxides, in general at from about 50 to about 150° C., preferably at from about 80 to about 130° C., in the presence or absence of regulators, eg. mercaptoethanol, tert-dodecyl mercaptan or diisopropyl xanthogen disulfide, which can be present in amounts from 0 to about 3% by weight, based on the sum total of monomers (I) to (III).

It is immaterial whether component (A) is polymerized first, and then component (B), or vice versa. In a preferred embodiment of the invention, however, component (A) is polymerized before component (B). The first polymerization is allowed to proceed to a substantial extent, ie. to an extent of preferably more than about 80%, especially more than about 90%, before the polymerization of the second component is commenced.

When the polymerization has ended, the solution comprising (A) and (B) is dispersed in water by addition of a base, for example ammonia, and so adjusted to non-Newtonian or plastic (Newtonian with yield point) flow rheo-logy. First a water-in-oil (WO) emulsion is formed since , the organic phase is not miscible with water, with the result of small water-droplets being emulsified in the organic phase. On continued addition of water or base, the WO emulsion inverts into a WOW emulsion at a certain phase ratio (aqueous phase/organic phase), the phase inversion point. Oil droplets (organic phase) are then emulsified in the aqueous phase which in turn enclose small volumes of water. The phase inversion point can be determined by conductivity measurements which are known to one of ordinary skill in the art.

In this connection, the formation of polymers having more than one void, or, more precisely, the formation of a WOW emulsion, is promoted by a high viscosity of the organic phase which is preferably within the range from about 10 to about 1000 Pa.s, more preferably within the range from about 50 to about 500 Pa.s, at a shear rate of 1/s (s=second) and a temperature of 80° C., and by cooling during the dispersing, so that a reaction procedure involving the use of an organic phase having the above-defined viscosity and simultaneous cooling during the dispersing is preferred.

The resulting mixture of components (A) and (B), having been neutralized with a base, preferably ammonia, is converted into a dispersion by addition of water.

The organic solvent or solvent mixture is then removed by distillation, the level of organic solvent in the final dispersion being preferably less than 5% by weight, especially less than 3% by weight, based on the amount of the dispersion.

The degree of neutralization of the resulting dispersion is generally within the range from about 10 to about 150%, preferably within the range from about 15 to about 100%, particularly preferably within the range from about 40 to about 70%. The pH of the dispersion can accordingly be within the range from about 6 to about 10, preferably within the range from about 7.0 to 9.0.

The polymer content of the dispersion of the present invention is advantageously chosen so that the viscosity of the dispersion is convenient for further processing. The polymer content is therefore generally within the range from about 25 to about 60% by weight, preferably within the range from about 30 to 40% by weight.

To obtain the polymer as a solid, the dispersion obtained after the removal of the organic solvent is dried, for example spray-dried, to remove the water.

The resulting polymer in dry form can then be stored and marketed and processed as a solid.

In addition, the polymer of the present invention, the dispersion of the present invention, the polymer prepared according to the invention and the dispersion prepared according to the invention, as defined above, can all be used as pigment and for microencapsulation.

For use as a pigment, the polymer or dispersion of the present invention is mixed with further components, for example a coating, for example binders and other coating assistants, to obtain a composition which includes the polymer of the present invention as a pigment.

For microencapsulation, the polymer or dispersion of the present invention is contacted with a suitable substrate, for example a pigment of a, for example, pharmacologic-ally or agrochemically active compound, the substrate then becoming included in the voids of the polymer of the present invention.

Accordingly, the present invention also provides a process for microencapsulating substrates by contacting a substrate with the polymer or dispersion of the present invention.

Accordingly, the present invention further provides a process For preparing a composition which includes the polymer of the present invention as a pigment by mixing the polymer or dispersion of the present invention with further components, as defined above, useful for preparing pigment compositions.

In addition, the present invention relates to the above-described compositions per se.

EXAMPLE 119 g of toluene and 51 g of n-octane were introduced as initial charge into a 4 liter reaction flask equipped with an anchor stirrer, a reflux condenser and two inlets and were heated up together with 182 g of feed 1, consisting of 75 g of acrylic acid and 425 g of styrene, to 105° C. under nitrogen. When 105° C. was reached, 15 g of a feed 3, consisting of 20 g of tert-butyl peroctoate, 161 g of toluene and 69 g of n-octane, were metered in over 2 minutes. The remainder of feed 1 (318 g) and 15 g of feed 3 were then metered in over 45 minutes. This was followed by 15 minutes of postpolymerization. Thereafter 135 g of feed 2 (500 g of styrene) and 30 g of feed 3 were metered in over two hours. This was followed by one hour of postpolymerization. Then the rest of feed 2 (365 g) and 130 g of feed 3 were metered in over three hours. Subsequently the rest of feed 3 was metered in over two hours, which was followed by two hours of postpolymerization.

The polymer solution was neutralized with 70.8 g of aqueous ammonia solution (25% strength by weight) at an external temperature of 70° C. The neutralized polymer solution was then dispersed with 1000 g of water stirred in over an hour.

835 g of a solvent/water mixture were distilled off under reduced pressure at an external temperature of 70° C. while at the same time 1200 g of fresh water were metered in.

The dispersion obtained had the following properties:
pH: 8.1
Solids content: 32.9%
Residual solvent content: 0.3%
Particle size: >1 to about 5 μm (determination by electron microscopy)

We claim:

1. A polymer mixture in the form of particles, consisting essentially of the components
   A) from 25 to 70% by weight of a copolymer A containing
      I) from 5 to 50% by weight of at least one copolymerizable monomer containing at least one hydrophilic group,
      II) from 20 to 95% by weight of at least one copolymerizable monomer which is free of hydrophilic groups,
      III) from 0 to 30% by weight of at least one other copolymerizable monomer,
      the percentages mentioned under I) to III) adding up to 100,
   B) from 30 to 75% by weight of a solution polymer B containing from 0 to less than 5% by weight of the above monomer I,
   obtainable by a process comprising the following steps:
      α) solution polymerization of one of said components (A) or (B) in an organic solvent and subsequent solution polymerization of the other component in the resulting polymerization solution, the solution polymerization being carried out in a water-immiscible solvent or solvent mixture,
      β) dispersing the solution comprising (A) and (B) in water in the presence of a base, and
      γ) distillative removal of the organic solvent down to a concentration of less than 5% by weight, based on the amount of the dispersion;
   wherein said particles are more than 1 μm in size and contain more than one void; and wherein said organic solvent is a mixture of a good solvent for the polymer mixture and a very poor solvent for the polymer mixture.

2. A polymer as claimed in claim 1, wherein said monomer I is selected from the group consisting of a copolymerizable olefinically unsaturated carboxylic acid or anhydride, a copolymerizable olefinically unsaturated sulfonic acid or a derivative thereof, a copolymerizable olefinically unsaturated sulfate, a copolymerizable olefinically unsaturated phosphoric acid or a derivative thereof, a copolymerizable olefinically unsaturated phosphonic acid or a derivative thereof, each having up to 10 carbon atoms, and a mixture of two or more thereof.

3. A polymer as claimed in claim 1, wherein said monomer II is selected from the group consisting of an alkyl (meth)acrylate ester having a $C_1$–$C_{20}$-alkyl radical, an aromatic vinyl compound and a mixture of two or more thereof.

4. A polymer as claimed in claim 1, wherein the size of the voids is within the range from 400 to 800 nm.

5. An aqueous dispersion comprising at least one polymer as claimed in claim 1.

6. A process for preparing an aqueous dispersion as defined in claim 5, comprising the following steps:
   α) solution polymerization of one of said components (A) or (B) in an organic solvent and subsequent solution polymerization of the other component in the resulting polymerization solution, the solution polymerization being carried out in a water-immiscible solvent or solvent mixture,
   β) dispersing the solution comprising (A) and (B) in water in the presence of a base, and
   γ) distillative removal of the organic solvent down to a concentration of less than 5% by weight, based on the amount of the dispersion.

7. A process for preparing a polymer as defined in claim 1 in the form of a solid, comprising the following steps:
   α) solution polymerization of one of said components (A) or (B) in an organic solvent and subsequent solution polymerization of the other component in the resulting polymerization solution, the solution polymerization being carried out in a water-immiscible solvent or solvent mixture,
   β) dispersing the solution comprising (A) and (B) in water in the presence of a base, and
   γ) distillative removal of the organic solvent down to a concentration of less than 5% by weight, based on the amount of the dispersion, and
   δ) subsequent drying of the dispersion.

8. A process for preparing a pigment composition, which comprises mixing a polymer as defined in claim 1 or a dispersion as defined in claim 5 with a coating for preparing pigment compositions.

9. A process for microencapsulating a substrate, which comprises contacting the substrate with the inventive polymer as defined in claim 1 or the inventive dispersion as defined in claim 5.

* * * * *